(12) United States Patent
Kurihara et al.

(10) Patent No.: US 11,351,070 B2
(45) Date of Patent: Jun. 7, 2022

(54) ABSORBENT ARTICLE FOR INCONTINENCE

(71) Applicant: DAIO PAPER CORPORATION, Ehime (JP)

(72) Inventors: Ryoko Kurihara, Tochigi (JP); Junta Tagomori, Tochigi (JP); Mariko Nagashima, Tochigi (JP)

(73) Assignee: DAIO PAPER CORPORATION, Ehime (JP)

( * ) Notice: Subject to any disclaimer, the term of this patent is extended or adjusted under 35 U.S.C. 154(b) by 569 days.

(21) Appl. No.: 16/330,168

(22) PCT Filed: Sep. 7, 2017

(86) PCT No.: PCT/JP2017/032227
§ 371 (c)(1),
(2) Date: Mar. 4, 2019

(87) PCT Pub. No.: WO2018/047897
PCT Pub. Date: Mar. 15, 2018

(65) Prior Publication Data
US 2019/0183691 A1 Jun. 20, 2019

(30) Foreign Application Priority Data

Sep. 7, 2016 (JP) .............................. JP2016-174213

(51) Int. Cl.
| | | |
|---|---|---|
| *A61F 13/15* | (2006.01) | |
| *A61F 13/512* | (2006.01) | |
| *A61F 13/511* | (2006.01) | |
| *A61F 13/47* | (2006.01) | |
| *A61L 15/42* | (2006.01) | |

(52) U.S. Cl.
CPC ............ *A61F 13/512* (2013.01); *A61F 13/47* (2013.01); *A61F 13/511* (2013.01); *A61F 13/51104* (2013.01); *A61F 2013/15121* (2013.01); *A61L 15/42* (2013.01)

(58) Field of Classification Search
CPC ...................... A61F 2013/15121; A61L 15/42
See application file for complete search history.

(56) References Cited

U.S. PATENT DOCUMENTS

| | | | |
|---|---|---|---|
| 2002/0064639 A1 | 5/2002 | Rearick et al. | |
| 2002/0188267 A1 | 12/2002 | Wada et al. | |
| 2014/0343524 A1 | 11/2014 | Tokita et al. | |

FOREIGN PATENT DOCUMENTS

| | | |
|---|---|---|
| JP | 2003-102772 | 4/2003 |
| JP | 2010-269029 | 12/2010 |

(Continued)

OTHER PUBLICATIONS

JP 2010269029 J-Plat Pat translation (Year: 2010).*
International Search Report dated Oct. 31, 2017 in International Application No. PCT/JP2017/032227.

*Primary Examiner* — Jacqueline F Stephens
(74) *Attorney, Agent, or Firm* — Wenderoth, Lind & Ponack, L.L.P.

(57) ABSTRACT

In an absorbent article for incontinence using cotton fiber for a front-surface sheet, a diffusing range of liquid in the front-surface sheet is made to be a predetermined range or less, thereby eliminating a sticky feeling of the surface, and reducing water retention of the front-surface sheet so as to cause urine to diffuse in the front-surface sheet rapidly.

6 Claims, 6 Drawing Sheets

(56) References Cited

FOREIGN PATENT DOCUMENTS

| JP | 2010-279621 | | 12/2010 | | |
| JP | 2010269029 | * | 12/2010 | ............. | A61F 13/15 |
| JP | 2016-112155 | | 6/2016 | | |
| JP | 2016-221237 | | 12/2016 | | |

* cited by examiner

[Fig. 1]
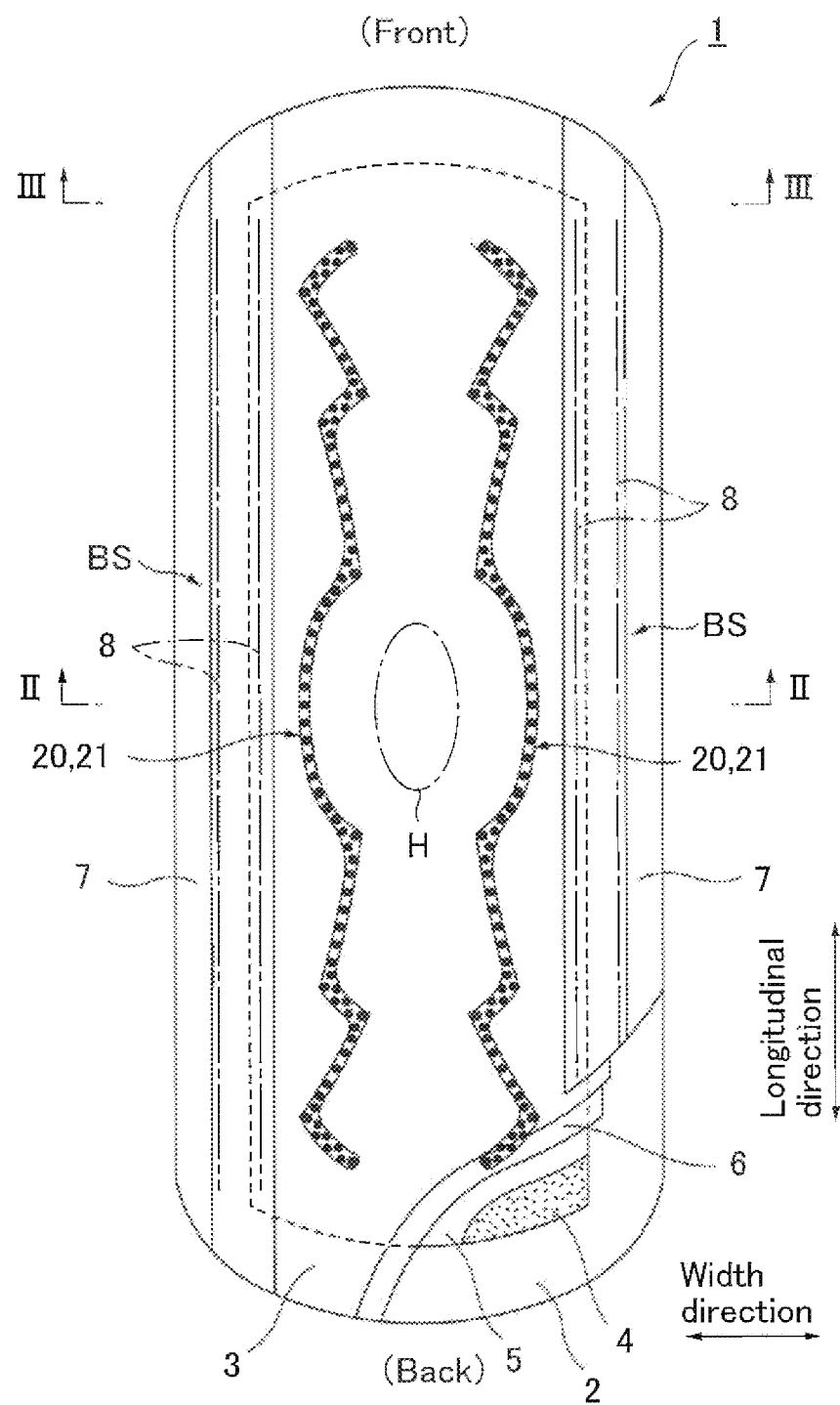

[Fig. 2]
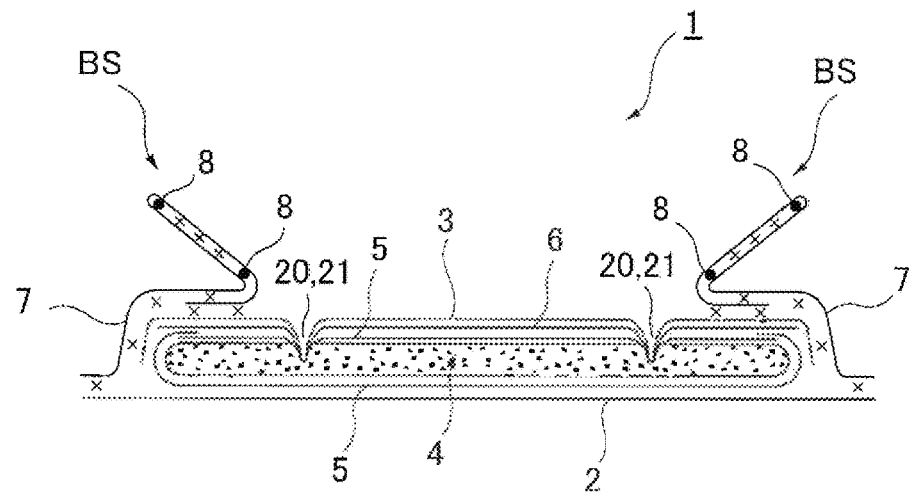
[Fig. 3]
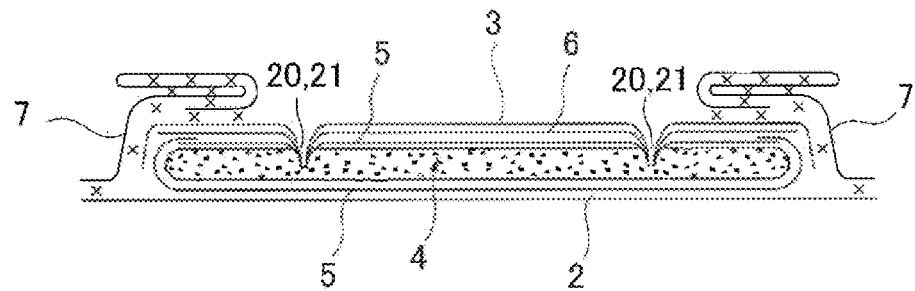

[Fig. 4]
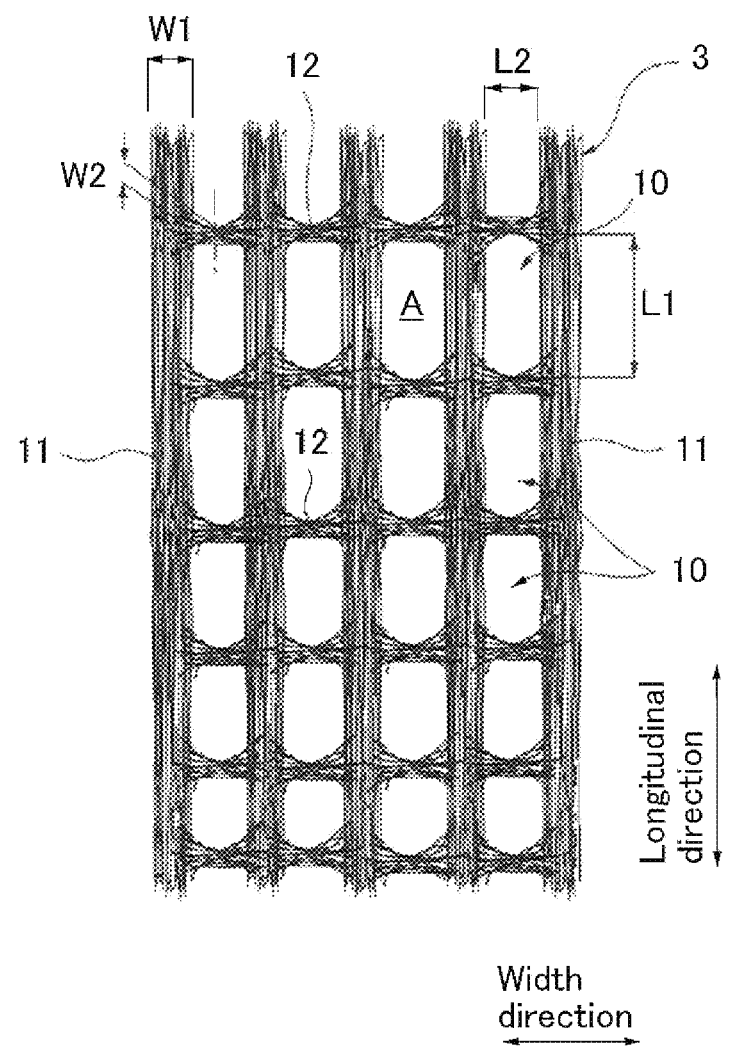

[Fig. 5]
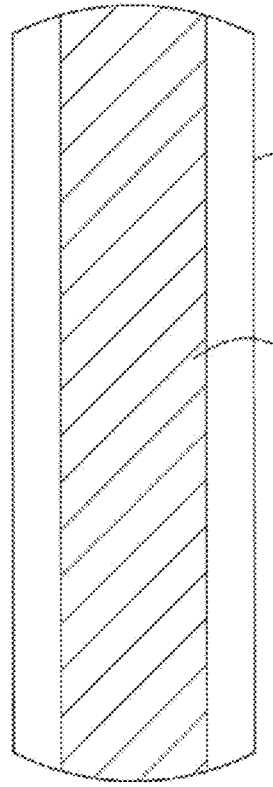
(A)
(Front)
(Back)
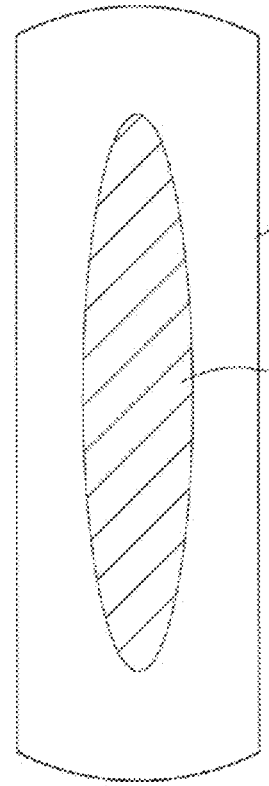
(B)
(Front)
(Back)
Longitudinal direction
Width direction

[Fig. 6]
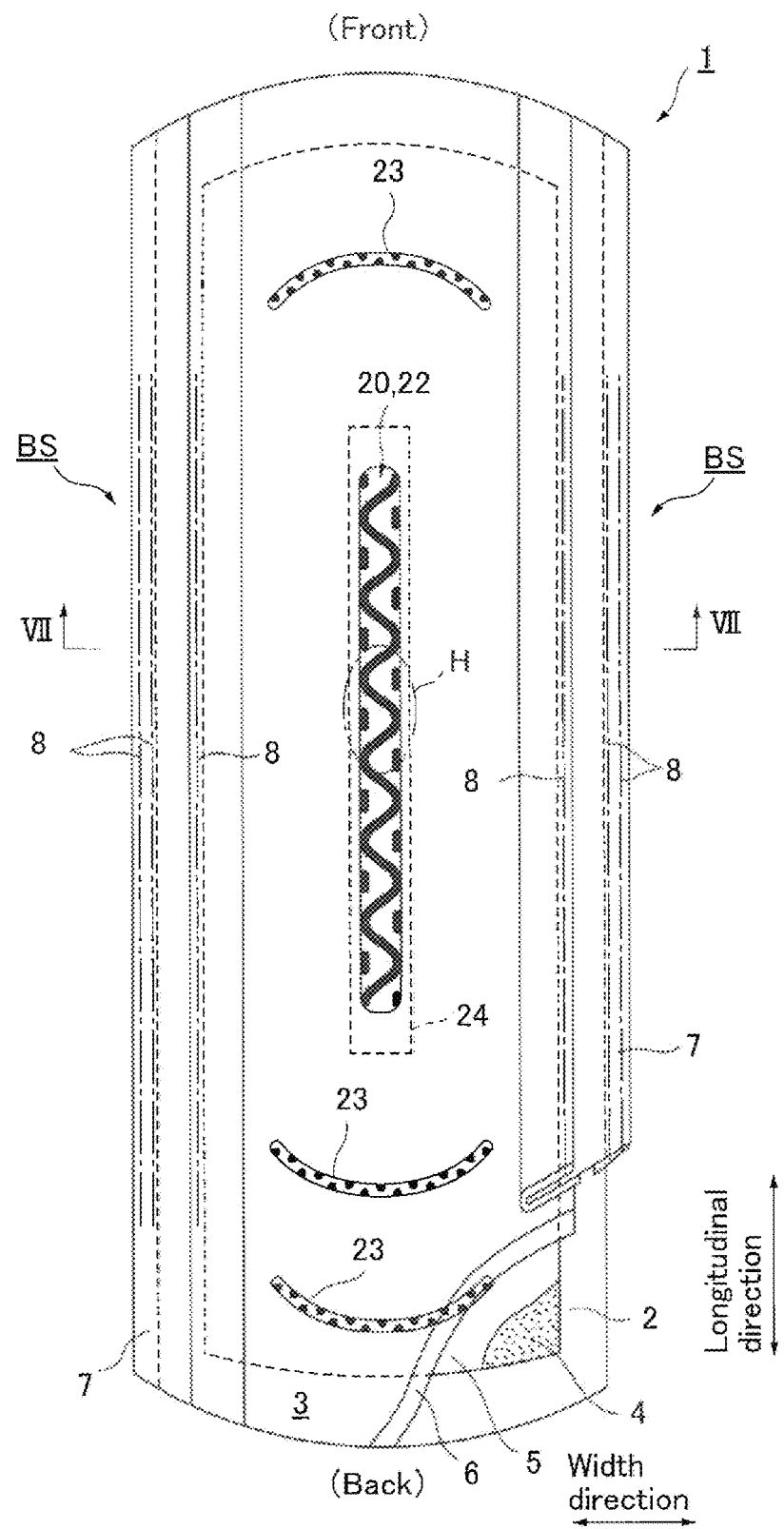

[Fig. 7]
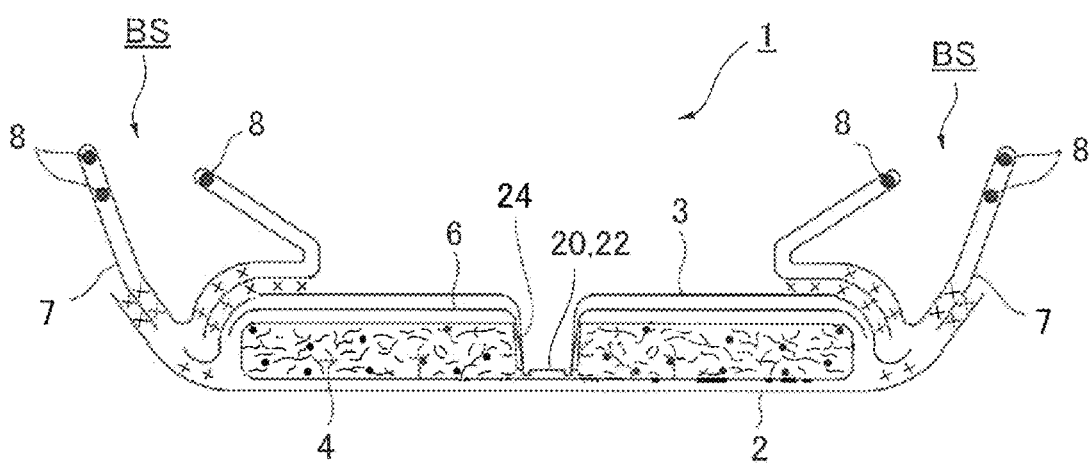

ABSORBENT ARTICLE FOR INCONTINENCE

FIELD OF THE INVENTION

The present invention relates to an absorbent article for incontinence mainly used for an incontinence pad, a light incontinence pad, an incontinence liner, a urine absorption pad, and the like, and relates to an absorbent article for incontinence for medium or larger volume, which absorbs a total urine volume of 20 cc or more.

DESCRIPTION OF RELATED ART

Conventionally, as absorbent articles for women, for example, incontinence pads, vaginal discharge sheets, panty liners, and sanitary napkins, absorbent articles including an impermeable back-surface sheet such as a polyethylene sheet or a polyethylene sheet-laminated nonwoven fabric and a front-surface sheet with an absorber made of paper cotton such as pulverized pulp interposed between the back-surface sheet and the front-surface sheet are known.

The front-surface sheet forms a skin-contact surface and accordingly is required to be soft, to be able to achieve a dry feeling on skin even after absorption of an excreted liquid, to have little irritation to the skin, or the like. As materials that satisfy such requirements, nonwoven fabrics of synthetic fibers and resin mesh sheets are broadly employed in the field of absorbent articles, particularly in the field of absorbent articles for incontinence. However, there was a problem that the front-surface sheet made of synthetic fiber causes itchiness, rash, or the like.

In order to solve this problem, a front-surface sheet made of cotton fiber (cotton) as a raw material has been proposed. In absorbent articles, a front-surface sheet is desired to have high liquid permeability and to allow liquid to rapidly reach the absorber. Meanwhile, there was a problem that when ordinary degreased cotton fiber is contained in the front-surface sheet, the front-surface sheet itself has high liquid retention properties and a sticky feeling easily remains on a surface.

Furthermore, an absorbent article having a front-surface sheet made of cotton fiber has an advantage of being capable of providing a soft feeling like underwear on the skin. However, as described above, since such an absorbent article has high liquid retention properties, when a large volume of body fluid is discharged, the body fluid remains in the front-surface sheet. Long-time wearing of the absorbent article may cause a moist feeling or rash. Therefore, in the conventional absorbent articles, when the cotton fiber is used in the front-surface sheet, its use was limited to products such as vaginal discharge sheets in which an absorption volume of the body fluid is small.

Examples of such absorbent articles using a cotton fiber in the front-surface sheet include Patent Literature 1 below. Patent Literature 1 below discloses an absorbent article including a top sheet obtained by applying a water repellent agent to spunlace nonwoven fabric made of 40 to 100% by weight of cotton fiber and 60 to 0% by weight of synthetic fiber, in which water absorbency of a skin-contact surface is 0 mm to 5 mm, and many openings penetrating from front to back are provided in at least an excretion hole part. According to such absorbent articles, employment of the spunlace nonwoven fabric having high cotton fiber content as the top sheet provides many advantages of the cotton fiber such as providing excellent skin contact and being difficult to cause itchiness or rash. Furthermore, residual liquid on a surface, which is a problem at this time, is sufficiently resolved by securing water absorbency of the skin-contact surface at a sufficiently low level by the application (external addition) of the water repellent agent. However, if the water absorbency is only made low, a liquid portion of the excreted matter cannot easily permeate through the top sheet, which causes lateral leakage or the like. Therefore, in the absorbent article described in Patent Literature 1, many openings penetrating from front to back are provided in at least the excretion hole part in the top sheet so as to make it possible to speedily absorb the liquid. As a result, Patent Literature 1 mentions advantageous effects that, for example, a sticky feeling due to residual liquid on the surface may be sufficiently prevented, and absorbed excreted liquid cannot easily return to a front-surface side of the top sheet due to the water repellency of the top sheet. Furthermore, Patent Literature 1 mentions that an application amount of the water repellent agent is 0.05 to 0.15 parts by weight relative to 100 parts by weight of fiber of the top sheet. This is because when the application amount is less than 0.05 parts by weight, the water repellent effect may be insufficient, and when the application amount is more than 0.15 parts by weight, the water repellent properties are too high, thus making it difficult to allow water to permeate.

CITATION LIST

Patent Literature

Patent Literature 1: JP-A-2010-269029

SUMMARY OF THE INVENTION

Technical problem

As mentioned in Patent Literature 1 that an application amount a water repellent agent is 0.15 parts by weight or less, in conventional absorbent articles, an application amount of a water repellent agent is generally at most 0.3 parts by weight or less relative to 100 parts by weight of fiber of the front-surface sheet. This is because when the application amount is more than 0.3 parts by weight, the water repellency of the front-surface sheet is excessively high, thereby making it difficult for water to permeate the front-surface sheet.

However, in the case of an absorbent article for incontinence, which uses a spunlace nonwoven fabric made of 100% by weight of cotton fiber as the front-surface sheet, since the front-surface sheet has high liquid retention properties as described above, when an application amount of a water repellent agent is small, urine absorbed by the front-surface sheet diffuses in a plane direction of the front-surface sheet, a diffusing range of the front-surface sheet is increased, and a range of the surface which causes a sticky feeling is enlarged to give discomfort to a wearer.

Furthermore, the diffusing range of liquid in the front-surface sheet is one indication of determining whether the discharged body fluid can permeate the front-surface sheet without being retained by the front-surface sheet. By suppressing this diffusing range so as to be small, liquid is not absorbed by the front-surface sheet, and rapidly passes through the front-surface sheet and is absorbed and retained by the absorber.

Thus, a main object of the present invention is to provide an absorbent article for incontinence using cotton fiber for a front-surface sheet wherein a diffusing range of liquid in the front-surface sheet is reduced to a predetermined range or less, thereby eliminating a sticky feeling on the surface, reducing water retention of the front-surface sheet, and allowing urine to permeate through the front-surface sheet rapidly.

Solution to Problem

In order to solve the above problem, as the present invention according to item 1, an absorbent article for incontinence is provided. The absorbent article for incontinence includes a front-surface sheet and a back-surface sheet with an absorber interposed therebetween.

The absorbent article for incontinence is an absorbent article for incontinence for medium or larger volume, which absorbs a urine volume of 20 cc or more.

The front-surface sheet is obtained by applying a water repellent agent to a spunlace nonwoven fabric made of 100% by weight of cotton fiber, has many openings penetrating from front to back in a region including an excretion hole corresponding part, and has a diffusion area of liquid of 2000 $mm^2$ or less based on the following diffusivity test:

<Diffusivity Test>
(1) Two sheets of qualitative filter paper cut into a size of 100 mm×100 mm are stacked on each other, and a front-surface sheet sample cut into a width of 80 mm×a length of 100 mm is placed thereon.
(2) 1 ml of tap water dyed blue is dropped using a pipette from a position 5 mm high from a surface of the front-surface sheet sample.
(3) After allowing to stand for 5 minutes, measurement of a diffusion area of a blue-dyed portion that spreads in the front-surface sheet sample is performed.
(4) The measurement is performed three times and an average value thereof is calculated.

In the invention described in item 1 above, when spunlace nonwoven fabric made of 100% by weight of cotton fiber is used as the front-surface sheet, one having a diffusion area of liquid in the front-surface sheet of 2000 $mm^2$ or less based on the diffusivity test above is used. Consequently, a range on the surface, in which a sticky feeling is generated by urine that diffuses in the front-surface sheet and is retained by the front-surface sheet, is reduced, and thus discomfort can be reduced. Furthermore, since the diffusion area of liquid in the front-surface sheet is a predetermined range or less, a flow of body fluid diffusing in the plane direction of the front-surface sheet is suppressed, the flow of the body fluid in the thickness direction easily occurs, the water retention in the front-surface sheet is reduced, and the liquid passes through the front-surface sheet rapidly and is absorbed and retained in the absorber.

In many cases, the absorbent article for incontinence is continuously used until the second incontinence, that is, it is worn for a long time in a state after the first incontinence, and it is disposed after urination again. Accordingly, in such an absorbent article for incontinence for medium or larger volume, a function of instantaneously absorbing and retaining a predetermined urine volume and maintaining a dry feeling on a surface is required.

Furthermore, in the absorbent article for incontinence for a medium or larger volume, which targets incontinence occurring when a force is applied to the abdomen, unless such conditions are met, the urination does not occur, and therefore, the absorbent article for incontinence may be worn for a long time in many cases. Therefore, the present absorbent article for incontinence uses a front-surface sheet obtained by applying a water repellent agent to a spunlace nonwoven fabric made of 100% by weight of cotton fiber, and having many openings penetrating from front to back in a region including an excretion hole corresponding part. Therefore, by employing the spunlace nonwoven fabric made of 100% by weight of cotton fiber, a soft feeling on the skin is obtained, skin trouble such as itchiness or rash during wearing does not easily occur even when wearing for a long time, and a moist feeling before urination can be reduced due to moisture absorbent properties of cotton fiber. The residual liquid on a surface as a problem at this time can be sufficiently resolved by application of the water repellent agent. Furthermore, since many openings penetrating from front to back are provided in a region of the front-surface sheet including the excretion hole corresponding part, the body fluid permeates speedily. When a formation region of the openings is formed in such a manner that the excretion hole corresponding part is not included, a situation in which an incontinence region cannot be covered occurs, urine remains in the front-surface sheet to easily cause a sticky feeling, and skin trouble such as itchiness or rash tends to occur during wearing.

As the present invention according to item 2, the absorbent article for incontinence according to item 1 is provided, in which an application amount of the water repellent agent is 0.3 parts by weight or more relative to 100 parts by weight of cotton fiber.

In the present invention described in item 2 above, in the front-surface sheet obtained by applying a water repellent agent to spunlace nonwoven fabric made of 100% by weight of cotton fiber, in order to make the diffusion area of liquid be 2000 $mm^2$ or less, the application amount of the water repellent agent is 0.3 parts by weight or more relative to 100 parts by weight of cotton fiber. This application amount is much larger than an application amount of a water repellent agent to be applied to the front-surface sheet used for usual absorbent articles whose surface material is made of cotton fiber. Consequently, the liquid retention properties of the front-surface sheet are greatly reduced, and after urine is absorbed by the absorber, reversion to the surface hardly occurs, the residual liquid on the surface is reduced, and the sticky feeling on the surface is eliminated.

At this time, when the application amount of the water repellent agent is increased, water repellency of the front-surface sheet is excessively high, resulting in difficulty for moisture to permeate as mentioned above. The present invention solves the problem as follows.

The present invention is directed to an absorbent article for incontinence for medium or larger volume, where the absorbent article for incontinence absorbs urine discharged instantaneously when a force is applied to the abdomen, for example, at the time of sneezing, coughing, or when holding a heavy object, or absorbs urine repeatedly discharged at night, and absorbs a total volume of 20 cc or larger. In the case where the target is a sanitary napkin, the body fluids to be absorbed are menstrual blood or vaginal discharge, and the discharged amount of the body fluids is small, and there is little momentum when the body fluids are discharged. Therefore, when the water repellency of the front-surface sheet is too high, it is difficult for moisture to permeate. However, the present invention is directed to an absorbent article for incontinence, and hence enables the urine to permeate through the front-surface sheet having high water repellency with a momentum of the urine at the time when the urine is discharged. Therefore, the present invention is clearly different from a sanitary napkin or the like for absorbing menstrual blood or vaginal discharge. The sanitary napkin is not included in the scope of the present invention.

Furthermore, in the present absorbent article for incontinence, the amount of the water repellent agent to be applied is 0.3 parts by weight or more relative to 100 parts by weight of cotton fiber, whereby the cotton fiber is provided with a flexible feeling and water repellency, and, in particular, softness of the front-surface sheet before urine is discharged is improved.

As the present invention according to item 3, the absorbent article for incontinence according to item 1 or 2 is provided, in which the front-surface sheet is made of non-degreased cotton fiber.

According to the invention described in item 3 above, since the non-degreased cotton fiber is used for the front-surface sheet, natural fat and oil of cotton wax that adheres to a surface of the cotton fiber makes it more difficult for the front-surface sheet to absorb the body fluid.

As the present invention according to item 4, the absorbent article for incontinence according to any one of items 1 to 3 is provided, in which the absorber includes a pulp fiber that does not include synthetic fiber and a superabsorbent polymer in a ratio of the pulp fiber:the superabsorbent polymer as 0 to 70% by weight: 100 to 30% by weight.

In the absorbent article described in Patent Document 1 above, attempt has been made to reduce the liquid retention properties in the front-surface sheet by improving the water repellency or permeability of the front-surface sheet. However, depending on properties of the absorber, when a content ratio of the superabsorbent polymer is excessively low, reversion may occur due to poor liquid retention properties of the absorber. When cotton fiber is used in the front-surface sheet, the reversed urine is likely to remain on a surface, which may further promote the sticky feeling.

Thus, in the invention described in item 4 above, through the use of an absorber including a superabsorbent polymer at a predetermined weight ratio or more, even when the urine is instantaneously discharged, by causing the pulp fiber having a high absorption speed to rapidly absorb urine immediately after the urination or by causing the urine to be retained in gaps among superabsorbent polymer particles whereafter the body fluid is gradually absorbed by the superabsorbent polymer and retained therein, reversion to the surface is prevented. Furthermore, since the urine is securely absorbed and retained in the absorber immediately after the urination and the residual liquid on the front-surface sheet is reduced, the diffusion range of the urine in the front-surface sheet can be reduced.

It is well known that the absorber includes pulp fiber and a superabsorbent polymer. In particular, however, as in the present invention, under the conditions where the front-surface sheet is formed of the spunlace nonwoven fabric made of 100% by weight of cotton fiber to which a water repellent agent is applied, and has many openings penetrating from front to back formed in a region containing the part corresponding to the excretion hole, it is considered that the optimum ranges of blending ratios of the pulp fiber and the superabsorbent polymer are different from the case where a nonwoven fabric or a mesh sheet made of an olefin-based resin such as polyethylene or polypropylene is used as the front-surface sheet.

In general, in a water absorption mechanism when the absorber is formed of a pulp fiber and a superabsorbent polymer, although the superabsorbent polymer exhibits by itself an astounding absorption power, there are problems such as that the water-absorbing power cannot be exhibited if it is not wetted to some extent and that the absorption speed is slow; therefore, the pulp fiber having an absorption speed remarkably greater than that of the superabsorbent polymer absorbs instantaneously and belatedly to this, an absorption form is adopted in which the urine retained between gaps of the pulp fibers moves to the super absorbent polymer side. Furthermore, when the absorber is formed of a polymer sheet that supports a superabsorbent polymer between hydrophilic sheets, discharged urine penetrates into and is retained in gaps among the super absorbent polymer particles or into and in the hydrophilic sheet. Furthermore, when an intermediate sheet made of hydrophilic nonwoven fabric and the like is arranged between the front-surface sheet and the polymer sheet, if necessary, discharged urine also penetrates into the intermediate sheet and is retained. Then, belatedly to this, urine that has been retained in the polymer particles, the hydrophilic sheet, and the intermediate sheet moves toward the superabsorbent polymer side. Note here that it is possible to use an absorber that combines the polymer sheet with the absorber including the pulp fiber and the superabsorbent polymer.

Accordingly, in the invention of the present application, in order to satisfy, with good balance, all of rapid absorption performance immediately after the urination, prevention performance against reversion to the surface after absorption of the urine by the absorber, and residual liquid reduction performance in the front-surface sheet, a ratio of the pulp fiber to the superabsorbent polymer is set as the pulp fiber:the superabsorbent polymer=0 to 70% by weight:100 to 30% by weight.

When the blending ratio of the pulp fiber is more than 70% by weight, and the blending ratio of the superabsorbent polymer is less than 30% by weight, since the content ratio of the pulp fiber becomes higher, the liquid retention properties of the absorber are low, and there is concern that the reversion to the front-surface sheet may occur after the urination.

As the present invention according to item 5, the absorbent article for incontinence according to item 4 is provided, in which a basis weight of the pulp fiber is 0 to 800 g/m$^2$, and a basis weight of the superabsorbent polymer is 85 to 800 g/m$^2$.

In the invention described in item 5 above, in order to secure the absorption volume of the absorber, the basis weight of the pulp fiber is set as 0 to 800 g/m$^2$ and the basis weight of the superabsorbent polymer is set as 85 to 800 g/m$^2$, where each is set so as to include basis weight in a high range. Thus, urine penetrating through the liquid permeable front-surface sheet can be reliably absorbed and retained by the absorber.

As the present invention according to item 6, the absorbent article for incontinence according to any one of items 1 to 5 is provided, in which the water repellent agent contains stearic acid amide.

The invention described in item 6 above uses one containing stearic acid amide (octadecanamide) as a water repellent agent, which is less irritating to the skin and less likely to cause skin troubles such as itchiness and rash.

As the present invention according to item 7, the absorbent article for incontinence according to any one of items 1 to 6 is provided, in which the openings are provided in a region that is 15% or more of a length of the absorber in a longitudinal direction of the absorbent article for incontinence, and 50% or more of a width of the absorber in a width direction of the absorbent article for incontinence.

In the invention described in item 7 above, when a region in which the openings are formed is less than 15% of the length of the absorber in the longitudinal direction of the absorbent article for incontinence, and less than 50% of the width of the absorber in the width direction of the absorbent article for incontinence, a situation in which an incontinence region cannot be covered occurs, urine remains in the front-surface sheet to easily cause a sticky feeling, and skin trouble such as itchiness or rash tends to occur during wearing.

Advantageous Effect of Invention

As described in detail above, according to the present invention, in the absorbent article for incontinence using cotton fiber in the front-surface sheet, when a diffusing range of liquid in the front-surface sheet is made to be at a predetermined range or less, a sticky feeling on the surface is reduced, water retention in the front-surface sheet can be reduced, and urine can penetrate through the front-surface sheet rapidly.

BRIEF DESCRIPTION OF THE DRAWINGS

FIG. 1 is a partially broken development view of an incontinence pad 1 according to the present invention.
FIG. 2 is an arrow view taken along line II-II in FIG. 1.
FIG. 3 is an arrow view taken along line III-III in FIG. 1.
FIG. 4 is an enlarged plan view of a front-surface sheet 3.
FIG. 5 is a development view showing a water repellent agent application pattern on a surface of the front-surface sheet 3.
FIG. 6 is a partially broken development view of an incontinence pad 1 in accordance with a modification example.
FIG. 7 is an arrow view taken along line VII-VII in FIG. 6.

DESCRIPTION OF EMBODIMENTS

Hereinafter, an embodiment of the present invention will be described in detail with reference to the drawings.

The present invention is an absorbent article for incontinence such as an incontinence pad or an adult night urine absorption pad (hereinafter, referred to as an "incontinence pad 1") for medium or larger volume, suitable for absorbing urine in a total volume of 20 cc or more, preferably 20 cc to 2500 cc, in particular, about 100 cc to 350 cc, and is particularly suitable for absorbing urine that is instantaneously discharged when a force is applied to the abdomen, for example, when sneezing, coughing, or when holding a heavy object, or urine that is repeatedly discharged at night. The present invention is clearly different from a sanitary napkin, a vaginal discharge sheet, a panty liner, or the like, for absorbing menstrual blood or vaginal discharge. The sanitary napkin, vaginal discharge sheet, and panty liner are not included in the scope of the present invention. Body fluids to be absorbed by the sanitary napkin or the like are mainly menstrual blood, vaginal discharge, or the like. The menstrual blood and vaginal discharge have high viscosity, a discharged amount at one time is small, and a momentum at the time of discharge of the body fluids is small. Meanwhile, in the incontinence pad 1 according to the present invention, a body fluid to be absorbed is mainly urine. The urine has lower viscosity as compared with menstrual blood and vaginal discharge, the discharged amount at one time is large, and in particular, for example in the case of abdominal pressure urinary incontinence, a momentum at the time of discharge of the body fluid is increased. Therefore, the incontinence pad 1 focuses on such a difference of discharge of body fluids, and has a configuration specialized in absorbing urine.

<One Example of Basic Structure of Incontinence Pad>

An incontinence pad 1 according to the present invention mainly includes, as shown in FIGS. 1 to 3, an impermeable back-surface sheet 2 made of, for example, a polyethylene sheet, a front-surface sheet 3 that forms a skin-contact surface and allows rapid permeation of urine or the like, an absorber 4 interposed between both sheets 2 and 3 and made of cotton pulp or synthetic pulp, and a pair of right and left three-dimensional gathers BS and BS provided to protrude with a substantial lateral edge part of the absorber 4 as a rise-up base edge to a skin side within a predetermined interval in the front-back direction so as to contain at least a urination hole part H of a wearer. In the surrounding of the absorber 4, at upper and lower end edge parts thereof, outer edge parts of the impermeable back-surface sheet 2 and the front-surface sheet 3 are joined by an adhesive such as a hot melt or by adhering means such as a heat seal; furthermore, at both lateral edge parts thereof, the impermeable back-surface sheet 2 that extends further on the lateral side than the absorber 4 and a side non-woven fabric 7 that forms the three-dimensional gather BS are joined with an adhesive such as a hot melt or by adhering means such as a heat seal. In an illustrated example, the absorber 4 is formed in a single-layer structure but may be formed in a multi-layered structure that forms a center high part, and also may be formed in a multi-layered structure in which absorbers having the same size and shape are stacked.

In the impermeable back-surface sheet 2, a sheet material having at least water-blocking properties, for example, polyethylene is used. In recent years, however, from the viewpoint of preventing a moist feeling, a sheet material having moisture permeability has tended to be used. As the water-blocking and moisture-permeable sheet material, a microporous sheet obtained by molding a sheet by melting and kneading an inorganic filler in an olefin-based resin such as polyethylene or polypropylene, followed by stretching in uniaxial or biaxial direction is suitably used. On an unused surface side (outside surface) of the impermeable back-surface sheet 2, one or a plurality of stripes of adhesive layers (not shown in the drawing) are formed, and the incontinence pad 1 is fixed to underwear when wearing on the body. As the impermeable back-surface sheet 2, a polylaminated nonwoven fabric in which a plastic film and a nonwoven fabric are laminated may be used.

In the illustrated example, the front-surface sheet 3 is formed in a width to an extent that the front-surface sheet 3 has a width slightly larger than a width of the absorber 4 and only covers the absorber 4. The outside in the width direction of the front-surface sheet 3 is covered by the side nonwoven fabric 7 (a member other than the front-surface sheet 3) that extends from surfaces of both side parts of the front-surface sheet 3. A part on a center side in the width direction of the side nonwoven fabric 7 forms a three-dimensional gather BS. As the side nonwoven fabric 7, in response to objectives such as prevention of permeation of urine or enhancement of a feeling on the skin, a nonwoven fabric material to which appropriate water repelling treatment or hydrophilic treatment is applied can be used. As such side nonwoven fabric 7, one formed by a suitable processing method using a natural fiber, a synthetic fiber or a recycled fiber as a raw material can be used. However, preferably, in order to eliminate a stiff feeling and to prevent a moist feeling, a nonwoven fabric having aeration properties with the basis weight suppressed may be used. Specifically, a nonwoven fabric produced by setting the basis weight at 15 to 23 g/m² is desirably used, and in order to securely prevent permeation of the body fluid, a water-repellent nonwoven fabric coated with a water repellent agent, such as a silicon-based or paraffin-based water repellent agent, or the like is suitably used.

As shown in FIGS. 2 and 3, the side nonwoven fabric 7 adheres to an outside portion further outside than an intermediate portion in a width direction with an adhesive such as a hot melt over a range from an inside position of the absorber 4 to an outer periphery of the impermeable back-surface sheet 2 slightly exceeding an absorber side edge.

On the other hand, an inner side portion of the side nonwoven fabric 7 is folded substantially into two fold and in the inside of the two-folded sheet, one or a plurality of thread-like elastic stretchable members, two thread-like elastic stretchable members 8 and 8 in the illustrated example, in which both ends or appropriate positions at both ends in the longitudinal direction are fixed in the intermediate part in the height direction of the two-folded sheet, are arranged in a state in which both ends or an appropriate position in the longitudinal direction are fixed. The double-folded sheet parts, in the front and back end parts, are fixed to a front-surface sheet 3 side in a folded state as shown in FIG. 3.

<Front-Surface Sheet>

The front-surface sheet 3 forms a skin-contact surface that is a part that covers a skin side of the absorber 4 and is constituted by a spunlace nonwoven fabric made of 100% by weight of cotton fiber. The spunlace nonwoven fabric has advantages, such as that it does not use an adhesive and that it has flexibility.

The nonwoven fabric of the front-surface sheet 3 uses cotton fiber alone and does not include a synthetic fiber. As the cotton fiber, any cotton fibers can be used, and examples thereof include raw cotton of cotton, refined/bleached cotton fiber or dyed cotton fiber after refining/bleaching, refined/bleached and degreased cotton fiber, and further, recovered wool obtained by fibrillating one that was formed into thread or cloth. In particular, non-degreased cotton provided with a slight water repellency even in a state of fiber due to natural fat of cotton wax that adheres to a surface of the cotton fiber is preferably used.

The basis weight of the front-surface sheet 3 is set at 20 to 40 g/m$^2$, preferably at 27 to 34 g/m$^2$, and more preferably at 29 to 32 g/m$^2$, and a thickness is set at 0.25 to 0.50 mm, and preferably at 0.3 to 0.4 mm. The basis weight is calculated by measuring a weight of 10 sheets each having a size of 5 cm×30 cm with an electronic balance followed by converting into units per one square meter. Furthermore, the thickness is obtained according to JIS-L 1906.

As shown in FIG. 4, the front-surface sheet 3 is provided with many openings 10, 10 . . . penetrating from front to back to enhance the permeability. Specifically, the openings 10 can be formed by causing a fiber material to be carried on a mesh-like support in a stream interlacing process during manufacture of the spunlace. In this case, by changing a condition of the mesh to be used, an individual opening size and an opening rate can be adjusted. Of course, the openings may be formed by punching the nonwoven fabric after manufacture. The openings 10 may be provided over the entire front-surface sheet but are be formed in a region including at least an excretion hole corresponding part H. The openings 10 are preferably provided in a region that includes the excretion hole corresponding part H, is 15% or more of the absorber length in a product length direction, and 50% or more of the absorber width in a product width direction; and, more preferably, in a region that includes the excretion hole corresponding part H, is 50% or more of the absorber length in the product length direction, and 70% or more of the absorber width in the product width direction. When a formation region of the openings is less than 15% of the absorber length in the product length direction, and less than 50% of the absorber width in the product width direction, a situation where the incontinence region cannot be covered occurs, the urine remains on the front-surface sheet 3 to cause a sticky feeling, and a skin trouble such as itchiness or rash tends to occur during wearing.

Since as the front-surface sheet 3, one obtained by applying the water repellent agent to the spunlace nonwoven fabric made of 100% by weight of cotton fiber, and having many openings penetrating from front to back in the region including the excretion hole corresponding part H is used, a soft feeling on the skin is obtained, skin trouble such as itchiness or rash during wearing does not easily occur even when wearing for a long time, and a moist feeling before urination can be reduced due to moisture absorbent properties of cotton fiber. The residual liquid on a surface, which is a problem at this time, may be sufficiently resolved by application with the water repellent agent. Furthermore, since openings penetrating from front to back are provided in a region of the front-surface sheet 3 including the excretion hole corresponding part H, the body fluid permeates rapidly through the front-surface sheet via these openings.

As shown in FIG. 4, each of the openings 10 is formed in a vertically long shape that is long in the longitudinal direction of the incontinence pad 1. Therefore, since the body fluid can more readily permeate through these openings 10 than through circular openings, the urine can easily permeate through the front-surface sheet 3 via these openings 10, and water retained in the front-surface sheet 3 is reduced. Furthermore, when the urine permeates through the openings 10, since the liquid passes through while being transformed into a vertically long shape, a diffusion direction of the urine can be controlled toward a pad longitudinal direction, diffusion in the lateral direction is suppressed, and it becomes difficult for lateral leakage to occur. Note here that, although it is difficult for the shape of openings to become uniform in the case of the spunlace, a shape of the opening 10 becomes a shape like a substantial rectangle to a truncated long hole shape or an elliptical shape.

As dimensions of the opening 10, a length L1 in the longitudinal direction of the incontinence pad 1 may be set at 1.0 to 4.0 mm and preferably 1.5 to 3.0 mm, and a length L2 in the width direction of the incontinence pad 1 may be set at 0.5 to 1.5 mm and preferably 0.5 to 1.0 mm. When a dimension of the opening 10 is smaller than 0.5 mm, it is difficult for the urine to permeate through and it is difficult for a clear opening to be formed due to fluffing of the fiber. When a maximum dimension of the opening 10 exceeds 4.0 mm, the reversion of liquid from the opening 10 and surface exposure of a constituent material of the absorber 4 may be caused. Furthermore, a ratio of L1 and L2 (L1/L2) may be set at 1.2 to 5.0, and preferably 2.0 to 3.0. An area A of the opening 10 may be set at 0.9 to 3.0 mm$^2$ and preferably 0.9 to 2.5 mm$^2$. Furthermore, the opening rate may be set at 15 to 45%, preferably 17 to 30% and more preferably 18 to 25%. The dimensions of the opening 10 are not necessarily uniform over an entirety but may be formed in arbitrary dimensions as long as they are within the above range.

As shown in FIG. 4, the front-surface sheet 3 has a structure in which many vertical streaks 11, 11 . . . that extend along the longitudinal direction of the incontinence pad 1 and are formed with gaps in the width direction, and many lateral streaks 12, 12 . . . that extend along the width direction of the incontinence pad 1 and connect between adjacent vertical streaks 11, 11 that are formed with a gap in the longitudinal direction are formed by the cotton fiber, and the openings 10 are formed in a part surrounded by the vertical streaks 11 and lateral streaks 12.

A width W1 of the vertical streak 11 may be set at 0.5 to 2.5 mm and preferably 0.8 to 1.3 mm, and a width W2 of the lateral streak 12 may be set at 0.2 to 1.6 mm and preferably 0.3 to 0.7 mm. Furthermore, a ratio of the widths W1 and W2 (W1/W2) may be set at 1.2 to 2.0 and preferably 1.5 to 2.0. When the width W1 of the vertical streak 11 is made larger than the width W2 of the lateral streak 12, liquid diffusion in the longitudinal direction of the incontinence pad 1 along the vertical streak 11 tends to occur.

The vertical streak 11 includes a larger amount of fiber and is formed with a density higher than the lateral streak 12. Thereby, only parts of the vertical streaks 11 are brought into contact with the skin, and due to reduction of a contact area with the skin, skin trouble such as itchiness or rash during wearing is made to occur less easily even when wearing for a long time, and at the same time, the sticky feeling after the incontinence is alleviated. Furthermore, when the urine permeates through the front-surface sheet 3, due to a capillary action of the fiber, diffusion in the longitudinal direction of the incontinence pad 1 along the vertical streaks 11 having a relatively high density tends to occur. Furthermore, since the diffusion directions of the urine that permeates through the openings 10 and the urine that penetrates through the front-surface sheet 3 coincide in the longitudinal direction of the incontinence pad 1, the urine penetrates through the vertical streaks 11 of the front-surface sheet 3 so as to be pulled by the urine permeating through the openings 10. Thus, the residual liquid on the front-surface sheet 3 can be suppressed to as little as possible.

Measurement of the fiber amount can be carried out according to JIS P 8207 "Test method for classification of pulps with screens." Furthermore, measurement of the density can be carried out according to JIS P 8118 "Test method for thickness and density."

In the present incontinence pad 1, a recessed groove 20 is formed in an appropriate shape, recessed toward the non-skin side from the outer-surface side of the front surface sheet 3 to the absorber 4. The recessed groove 20 may be side embosses 21, 21 extending along the longitudinal direction of the incontinence pad 1 at least at both sides of the urination hole part H, respectively, as shown in FIGS. 1 and 2, or may be a center emboss 22 extending along the longitudinal direction including the urination hole part H at the center part in the width direction as shown in FIGS. 6 and 7. Whether the recessed groove 20 is the side emboss 21 or the center emboss 22 can be arbitrarily selected based on, for example, absorption capacity of urine, size of the incontinence pad 1, or amount of pulp or polymer. As one example, an incontinence pad 1 with a total length of 26 to 29 cm and an absorption capacity of about 100 to 130 cc can be set as a boundary; where for one smaller than this, the side emboss 21 can be employed, and for one larger than this, the center emboss 22 can be employed. The recessed groove 20 may include the side emboss 21 and the center emboss 22. In other words, the side embosses 21, 21 may be provided at both sides of the center emboss 22, apart from the center emboss 22.

It is preferable that the side emboss 21 is a recess-shaped groove that has been integrally recessed from the front-surface sheet 3 toward the absorber 4 by compression from the outer-surface side of the front-surface sheet 3.

Similar to the side emboss 21, the center emboss 22 may be a recess-shaped groove that has been integrally recessed from the front-surface sheet 3 toward the absorber 4 by compression from the outer-surface side of the front-surface sheet 3, or may be a recessed groove shape arranged such that the front-surface sheet 3 and the intermediate sheet 6 are disposed along an absorber recessed portion 24 that is recessed toward the non-skin side along the longitudinal direction at the center portion in the width direction including the urination hole part H, or along the absorber recessed portion 24 (or an absorber penetrating portion) of the absorber 4 provided with an absorber penetrating portion penetrating from the skin side toward the non-skin side, by compression from the outer-surface side of the front-surface sheet 3.

In the recessed groove 20, since each of the openings 10 formed in the front-surface sheet 3 is stretched in a pad width direction by compression from the outer-surface side of the front-surface sheet 3, urine can easily pass through the stretched openings 10. When each of the openings 10 is formed to be vertically long, that is longer in the pad longitudinal direction, the opening 10 having stretched in the pad width direction is opened more largely. Thus, the liquid-permeability is further improved.

In the front-surface sheet 3 made of 100% by weight of cotton fiber, it is preferable that the hot melt adhesive is mainly used for joining to the lower layer side because the front-surface sheet 3 is not thermally welded at the time of heat-embossing.

In addition to the side emboss 21 and the center emboss 22, width direction embosses may be provided so as to connect end portions of the side embosses 21, 21 at both sides, respectively, in the front and back portions in a region corresponding to the urination hole part H, whereby the region corresponding to the urination hole part H may be surrounded by recessed grooves (not shown). On the other hand, one width direction emboss 23 along the pad longitudinal direction or a plurality of width direction embosses 23 apart in the pad longitudinal direction may be provided in one or both regions apart in the pad longitudinal direction from the side emboss 21 or the center emboss 22 (see FIG. 6). Furthermore, although not shown in the drawings, one longitudinal direction emboss along the pad longitudinal direction or a plurality of longitudinal direction embosses apart in the pad longitudinal direction may be provided in one or both regions apart in the pad width direction from the side emboss 21 or the center emboss 22.

In the front-surface sheet 3, a diffusion area based on the following diffusivity test is set to be 2000 $mm^2$ or less, and preferably 1500 $mm^2$ or less. The diffusion area means an area seen in a plan view of the front-surface sheet 3 of diffusion in a plane direction of the front-surface sheet 3 when a liquid passes through the front-surface sheet 3.

<Diffusivity Test>
(1) Two sheets of qualitative filter paper (manufactured by ADVANTEC, Type: No. 2) cut into a size of 100 mm×100 mm are stacked on each other, and a front-surface sheet sample cut into a width of 80 mm×a length of 100 mm is placed thereon. Note here that a sheet width of the sample coincides with the width direction of the incontinence pad 1, the sheet length coincides with the length direction of the incontinence pad 1.
(2) 1 ml of tap water dyed blue with blue ink or paint is dropped using a pipette from a position 5 mm high from a surface of the front-surface sheet sample.
(3) After allowing to stand for 5 minutes, measurement of a diffusion area of a blue-dyed portion that spreads in the front-surface sheet sample is performed.
(4) The measurement is performed three times and an average value thereof is calculated.

Herein, the diffusion area can be measured by a method using software for analyzing an area from photographed image data, a method using an area measuring instrument for tracing an outline of a photographed picture to measure an area, and the like. Furthermore, the diffusion area can be calculated by the following diffusion area measurement method.

<Diffusion Area Measurement Method>
(1) The front-surface sheet sample and a ruler are photographed together, and printed onto A3 size paper.
(2) Based on the dimensions of the photographed ruler, the paper is cut into dimensions corresponding to a predetermined size (for example, 100 mm×100 mm) including an entire portion dyed blue (the weight of the cut paper having the predetermined dimensions is represented by X+Y).
(3) The portion dyed blue is cut out from the cut paper having the predetermined dimensions.
(4) A weight (X) of the cut-out portion dyed blue and a weight (Y) of the remaining paper having the predetermined dimensions are measured, respectively.
(5) The diffusion area is calculated with the following calculation formula.

Diffusion area=Entire area (100 mm×100 mm)× weight ($X$) of portion dyed blue of paper/weight ($X+Y$) of paper having predetermined dimension.

The above-mentioned diffusion area measurement method has advantages in that measurement can be performed easily and at a low price without using a special device or software.

The diffusion area changes depending on the application amount of the water repellent agent to the front-surface sheet 3, properties of the cotton fiber constituting the front-surface sheet 3, the dimensions and the opening rate of the surface sheet 3, the basis weight of the front-surface sheet 3, or the like. When the application amount of the water repellent agent is increased, the water absorption properties of the front-surface sheet 3 are reduced and the diffusion area is reduced. When the non-degreased cotton fiber is used, the water absorption properties are reduced and the diffusion area tends to be smaller as compared with the case where the degreased cotton fiber is used (see Examples mentioned later). Furthermore, it is considered that when the dimensions or the opening rate of the openings 10 are increased, the liquid-permeability is improved and the diffusion area is reduced; and that when the basis weight of the front-surface sheet 3 is reduced, the diffusion area is reduced.

When the diffusion area of liquid on the front-surface sheet 3 is made to be 2000 mm² or less, urine diffusing in the front-surface sheet 3 in the plane direction and retained in the front-surface sheet 3 at the time of urination can be reduced, and a range in which a sticky feeling of the surface by the retained urine is suppressed to a narrow range, so that discomfort during wearing can be reduced.

Furthermore, the diffusion area of liquid in the front-surface sheet 3 is a predetermined range or less, whereby the flow of the body fluid diffusing in the plane direction of front-surface sheet 3 is suppressed, the flow of the body fluid with respect to the thickness direction easily occurs, water retention in the front-surface sheet 3 is reduced, and liquid passes through the front-surface sheet 3 rapidly and is absorbed and retained in the absorber 4. The flow of the body fluid diffusing in the plane direction of the front-surface sheet 3 is suppressed because the application amount of the water repellent agent with respect to the front-surface sheet 3 is made to be a predetermined amount or more, the non-degreased cotton fiber is used as the cotton fiber constituting the front-surface sheet 3, the dimensions or the opening rate of the openings 10 provided in the front-surface sheet 3 are increased, the basis weight of the front-surface sheet 3 is reduced, and the like.

The water repellent agent is externally applied to the front-surface sheet 3. It is desirable that the application amount of the water repellent agent is 0.3 parts by weight or more relative to 100 parts by weight of cotton fiber, particularly 0.5 to 3.0 parts by weight, preferably 1.0 to 2.0 parts by weight, and more preferably 1.2 to 1.7 parts by weight (the total of the application amounts of both surfaces in the case where the water repellent agent is applied to both surfaces). The application amount is much larger as compared with the case where the application amount of a water repellent agent applied to the front-surface sheets of usual absorbent articles whose surface material is made of cotton fiber is 0.15 parts by weight. Therefore, even after the liquid retention properties of the front-surface sheet 3 are greatly deteriorated and urine is absorbed by the absorber 4, reversion to the surface hardly occurs, the residual liquid on the surface is reduced, and the sticky feeling on the surface is eliminated. When the application amount of the water repellent agent is 0.3 parts by weight or more, sufficient water repellent effects can be obtained, the diffusion area of the front-surface sheet 3 can be made to be 2000 mm² or less, reversion of the body fluid absorbed by the absorber and the residual liquid on the surface do not occur, and thus a sticky feeling is not felt. Furthermore, when the water repellent agent is 3.0 parts by weight or less, the moisture absorbent properties before urination become good, whereby a dry feeling can be maintained, and absorption of urine immediately after urination becomes good. Thus, the sticky feeling is not felt.

At this time, regarding the problem that increase in the application amount of the water repellent agent makes water repellency of the front-surface sheet 3 too high, and makes it difficult to allow moisture to penetrate, the present invention can solve the problem sufficiently by targeting an incontinence pad for medium or larger volume, absorbing urine discharged instantaneously when a force is applied to the abdomen at the time of, for example, sneezing, coughing, or holding a heavy object, or absorbing urine repeatedly discharged at night, and absorbing 20 cc or more, preferably, 100 cc or more, as mentioned above. When a subject includes also a sanitary napkin, body fluids to be absorbed include menstrual blood or vaginal discharge, viscosity is high, the discharged amount at one time is small, and a momentum at the time when the body fluid is discharged is small. Therefore, when the water repellency of the front-surface sheet is excessively high, it is difficult for menstrual blood or vaginal discharge to permeate. However, the present invention is directed to an incontinence pad, and the body fluid to be absorbed is mainly urine, has low viscosity, is discharged in a large amount at one time, and at a momentum at the time when the body fluid is discharged is large. Therefore, even when the water repellency of the front-surface sheet 3 is high, urine can easily permeate the front-surface sheet 3 by the momentum at the time of excretion of the body fluid. Furthermore, permeated urine is rapidly absorbed and retained by the absorber 4, and the reversion to the surface or the residual liquid on the surface occur with difficulty due to the high water repellency of the front-surface sheet 3. Thus, the dry feeling of the surface can be maintained.

Note here that the incontinence pad 1 is particularly preferably directed to an incontinence pad for medium to large volume, absorbing a urine volume of about 100 cc to 350 cc, but it can be used, without problem, as a urine absorption pad absorbing a urine volume of up to 2500 cc, or an incontinence pad for medium volume, absorbing a urine volume of about 20 cc to 100 cc.

In the present incontinence pad 1, one reason why urine can permeate through the front-surface sheet 3 even when the application amount of the water repellent agent is increased is as follows. In the incontinence pad 1, as described above, since the skin-contact surface is provided with a predetermined recessed groove 20 (emboss groove), urine flowing into this recessed groove 20 and temporarily retained therein can easily permeate through the front-surface sheet 3 via openings 10 formed on the bottom surface and the side surface of the recessed groove 20. Because the urine temporarily retained in the recessed groove 20 penetrates through not only the openings 10 formed in the bottom of the recessed groove 20 but also the openings 10 formed in the side surface, an opportunity for the urine to pass through the openings 10 is increased, thus allowing the urine to more easily penetrate through the front-surface sheet 3.

Forms of the recessed groove 20 include the side emboss 21 and the center emboss 22 as described above. In any embosses, since urine is temporarily retained in the recessed groove 20, the urine can pass through the front-surface sheet 3 via the openings 10 provided in the bottom surface and the side surface in the recessed grooves 20. With the center emboss 22, since it is provided in the center portion in the width direction, including the urination hole part H, urine discharged from the urination hole part H directly flows into the recessed groove 20. With the side emboss 21, side embosses 21 are provided at both sides of the region including the urination hole part H, respectively, though the inside part of the groin receives pressure (leg pressure) from the outside to the inside in the width direction when during wearing and the embosses on both sides are moved inward, whereby urine discharged to the center portion flows to the both sides and flows into the recessed groove 20. Due to such a difference in the flowing form of urine into the recessed groove 20, the center emboss 22 is preferably employed for an incontinence pad having relatively large capacity and the side emboss 21 is preferably employed for an incontinence pad having relatively medium capacity.

Furthermore, in the front-surface sheet 3 made of 100% by weight of cotton fiber, since the front-surface sheet 3 is not thermally melted by heat-embossing at the time of molding the recessed groove, the openings 10 are not blocked in the recessed groove 20, and the shape of the openings can be maintained. Therefore, urine passes through the openings 10 and is absorbed by the absorber 4 inside the recessed groove 20. Furthermore, as described above, since the shape of the openings can be maintained even with the heat-embossing at the time of molding the recessed groove, inside the recessed groove 20, by a compressive force when embosses are added inside the recessed groove 20, fibers constituting the intermediate sheet 6 disposed at the lower layer side enter the openings 10 of the front-surface sheet 3. Therefore, by the capillary action of fibers of the intermediate sheet 6 which the openings 10 face, urine is absorbed such as to be drawn and pulled, whereby the urine absorption effect in the recessed groove 20 can be further improved.

In addition to the urine being temporarily retained and absorbed by the recessed groove 20 as mentioned above, in the present incontinence pad 1 many openings 10 are provided in the front-surface sheet 3, whereby urine can easily pass through the front-surface sheet 3 via the openings 10 in a portion other than the recessed groove 20. Conventionally, it has been thought that if the application amount of the water repellent agent is excessively large, the water repellency of fiber becomes excessively strong, making it difficult for urine to permeate among fibers and reducing the liquid permeability of the front-surface sheet 3. However, in the case of the present front-surface sheet 3 made of spunlace nonwoven fabric made of 100% by weight of cotton fiber and having many openings 10 penetrating from front to back, when the water repellent agent is applied to some extent, although some urine passes among fibers, the proportion of urine passing through the openings 10 becomes high. Thus, even if the application amount of the water repellent agent is increased, the urine can permeate through the front-surface sheet 3 without problem. Furthermore, in the present incontinence pad 1, since the opening 10 has a vertically long shape that is longer in the longitudinal direction of the pad, when the incontinence pad 1 is curved along the roundness of the front and back of the body, the opening 10 is opened, and urine can pass with further ease.

As the water repellent agent, among known water repellent agents such as paraffin-based and silicone-based water repellent agents, one that is less irritant to the skin can be appropriately selected and used. However, it is more preferable to appropriately select and use less irritant oils and fats such as glyceryl stearate, stearic acid amide, zinc stearate, calcium stearate, stearic acid diethanol amide, and magnesium stearate. Among them, it is particularly preferable to use one containing stearic acid amide (octadecanamide). The stearic acid amide is advantageous in that it has particularly little irritation to the skin, and that skin trouble such as itchiness and rash does not easily occur, and is suitable in the present incontinence pad 1 whose application amount of the water repellent agent is increased. It is preferable that the water repellent agent includes a plurality of oils and fats blended, including animal oils and fats such as beef hydrogenated oil and vegetable oils and fats in addition to the stearic acid amide. Blending the beef hydrogenated oil has an advantage in that variation in the application of the water repellent agent can be reduced.

The water repellent agent may be applied only to a skin-contact surface or may be applied to both surfaces of the skin-contact surface and the surface on the absorber 4 side. However, it is preferable to at least make the water absorption amount obtained from a water absorption amount test described below to be 0.03 g or less, and preferably 0.02 g or less.

The water absorption amount of the front-surface sheet 3 was obtained according to the following procedure. (1) A sample of 10 cm×8 cm is prepared and a weight thereof is measured (A). (2) Two sheets of filter paper of 10 cm square are stacked with a smooth surface side upward, and the test sample is set thereon. (3) On the set sample, 1 ml of tap water at normal temperature is dropped, and is then left for 5 minutes. (4) A weight of the sample that has been left for 5 minutes is measured (B). (5) The water absorption amount (water retention amount) of the front-surface sheet 3 is obtained by (B)−(A)=water absorption amount (g).

In particular, it is more preferable that the water absorbency of a surface at the absorber 4 side is higher than the water absorbency at the skin-contact surface in the front-surface sheet 3. Therefore, the water absorbency (JIS L 1907 Byreck method) on the skin contact surface side is 0 mm to 5 mm, and preferably 0 mm to 2 mm, and the water absorbency (JIS L 1907 Byreck method) on the absorber 4 side is about 0 mm to 10 mm, and particularly preferably about 2 mm to 4 mm. Such a difference in the water absorbency can be easily obtained by applying the water repellent agent only on the skin-contact surface of the front-surface sheet 3, and can also be obtained by applying the water repellent agent on both surfaces of the front-surface sheet 3, where in this case, the water repellent agent is applied on the surface on the absorber 4 side in a smaller amount than on the skin-contact surface. Even when the water repellent agent is applied only on the skin-contact surface of the front-surface sheet 3, depending on the thickness or the basis weight, the surface on the absorber 4 side has water-repellency. Whether the water repellent agent is applied only on one surface or on both surfaces, or how a ratio of application amounts on both surfaces is set when applied on both surfaces can be appropriately selected such that, in addition to the conditions such as the thickness of the front-surface sheet 3, the basis weight, and openings, the water permeability and moisture absorbent properties can be held in a good balance.

As an application method of the water repellent agent, well-known methods such as a transfer method, a misting method, a brushing method, a soaking method, or a dipping method can be appropriately used. When a difference of water absorbance is provided between both surfaces of the sheet, an application method by transfer can be preferably used.

The water repellent agent is preferably applied over the entire surface from the viewpoint of production efficiency, but may be applied only on a part that receives the excreted liquid. For example, as shown in FIG. 5(A), a water repellent agent application part 40 may be provided excluding both side parts in the width direction. Furthermore, as shown in FIG. 5(B), the water repellent agent application part 40 may be provided only on a part central in the width direction and intermediate in the front-back direction.

<Absorber 4>

The absorber 4 can absorb and retain the urine, and the absorber 4 used is one in which particulate superabsorbent polymer is dispersed and mixed in fluffy pulp fiber. The absorber 4 is made of only the pulp fiber and the superabsorbent polymer and does not include the synthetic fiber.

Furthermore, as the absorber 4, a polymer sheet in which the particulate superabsorbent polymer is supported between two layers above and below of the hydrophilic sheets made of nonwoven fabric, paper, or the like, may be used. This polymer sheet includes only the superabsorbent polymer supported between the two layers of sheets and does not include the pulp fiber. An intermediate sheet made of hydrophilic nonwoven fabric or the like can be arranged between the pulp sheet and the front-surface sheet 3, if necessary.

Furthermore, as the absorber 4, a laminate in which an absorber made of pulp fiber and superabsorbent polymer is laminated on the skin side or the non-skin side of the polymer sheet may be used. A combination of the polymer sheet and the absorber including the pulp fiber and the superabsorbent polymer may be a laminate in which one layer of each is laminated, or one or both may be a of plurality of layers that are alternately laminated.

As the pulp fiber, one made of cellulose fibers such as chemical pulp obtained from timber or molten pulp, and artificial cellulose fibers such as rayon and acetate can be used; and one made of softwood pulp having a fiber length longer than hardwood pulp is suitably used from the viewpoint of function and price.

The basis weight of the pulp fiber is set at 0 to 800 $g/m^2$, preferably 75 to 800 $g/m^2$, and more preferably 300 to 550 $g/m^2$. The basis weight of the superabsorbent polymer is set at 85 to 800 $g/m^2$, and preferably 185 to 550$g/m^2$. One having the basis weight of the pulp fiber of 0 to 300 $g/m^2$ and the basis weight of the superabsorbent polymer of 85 to 200 $g/m^2$ is mainly targeted as an incontinence pad for a medium volume, absorbing a urine volume of about 20 cc to 100 cc. One having the basis weight of the pulp fiber of 0 to 800 $g/m^2$ and the basis weight of the superabsorbent polymer of 200 to 800 $g/m^2$ is mainly targeted as an incontinence pad or a urine absorption pad for medium to large volume, absorbing a urine volume of about 100 cc to 250 cc. This urine volume (absorbed amount) is only a standard, and may have a range of about ±30 cc. The basis weight of the pulp fiber and the basis weight of the superabsorbent polymer are an average of the entire absorber 4. When the basis weight of the superabsorbent polymer is set at 85 $g/m^2$ or more, in the incontinence pad 1 for a urine quantity of 20 cc or more, the water absorption amount is secured, and reversion to the surface or residual liquid on the surface is eliminated, thus eliminating the sticky feeling. On the other hand, when the basis weight of the pulp fiber is set at 800 $g/m^2$ or less, the absorber 4 is not too thick, and a problem of a stiff feeling in wearing does not occur. Furthermore, when the water absorption capacity of the absorber 4 is increased by increasing the basis weight of the superabsorbent polymer, the dry feeling can be improved. However, the basis weight of 800 $g/m^2$ or less eliminates a rough feel of the superabsorbent polymer before urination. Furthermore, the thickness of the absorber that has absorbed water and swelled is not too large, and worsening in the feel of wearing is prevented.

As the superabsorbent polymer, for example, a cross-linked polyacrylate, a self-crosslinked polyacrylate, a saponified product of an acrylic acid ester-vinyl acetate copolymer crosslinked product, an isobutylene/maleic anhydride copolymer crosslinked product, a crosslinked polysulfonate, or a product obtained by partially crosslinking a water-swelling polymer such as polyethylene oxide and polyacryl amide can be used. Among these, acrylic acid-based or acrylate-based polymers having excellent water absorption amounts and water absorption speeds are preferable. In the superabsorbent polymer having the water absorbance, the absorption rate (water absorption power) and absorption speed can be adjusted by adjusting a cross-linking density and a crosslinking density gradient in the production process of the superabsorbent polymer.

A ratio of the pulp fiber and the superabsorbent polymer is set at pulp fiber: superabsorbent polymer=0 to 70% by weight: 100 to 30% by weight. In the present incontinence pad 1, the pulp fiber and the superabsorbent polymer have predetermined basis weights, respectively, and an absorber including the pulp fiber and the superabsorbent polymer at a predetermined weight ratio is used. Consequently, even when the urine is instantaneously discharged, the pulp fiber or the intermediate sheet having high absorption speed rapidly absorbs the urine immediately after urination, and thereafter, the urine absorbed by the pulp fiber or the intermediate sheet is gradually absorbed by the superabsorbent polymer and retained therein. Thereby, the reversion to the surface can be prevented perfectly. Furthermore, since the urine is securely absorbed and retained in the absorber immediately after the urination, and the residual liquid does not occur in the front-surface sheet, expansion of a diffusion range of the urine in the front-surface sheet can be suppressed. In particular, when the blending ratio of the superabsorbent polymer is made to be high as 50% to 100%, by arranging the intermediate sheet between the front-surface sheet 3 and the absorber 4, if necessary, the excreted urine is caused to be absorbed and diffused in the intermediate sheet, and is then caused to be moved to the absorber 4, whereby after the absorber 4 absorbs the urine, reversion of the urine from the absorber 4 is preferably prevented.

On the contrary, when the pulp fiber is included in more than 70% by weight, since the content ratio of the pulp fiber becomes high, the liquid retention properties of the absorber 4 are low, and the reversion to the front-surface sheet 3 after urination tends to occur.

When the absorber 4 contains the pulp fiber, the absorber 4 is desirably surrounded by a wrapping sheet 5 such as crepe paper for shape retention, polymer powder retention, and the like.

<Intermediate Sheet>

The front-surface sheet 3 of the incontinence pad 1 according to the present invention has many openings 10. In order to prevent the pulp, polymer, adhesive, or the like, constituting the absorber 4 from being exposed from the openings 10, an intermediate sheet 6 is preferably provided between the front-surface sheet 3 and the absorber 4. The intermediate sheet 6 also has effects of preventing the reversion from the absorber 4, and of making a feel on the skin soft when wearing due to a cushion-like effect.

The intermediate sheet 6 of the examples of the drawings has a single layer structure but may have a two-layer structure by folding the intermediate sheet 6 into a tubular shape. The intermediate sheet 6 may be provided over an entire part of the skin-contact surface or may be provided only in a center in the width direction and on the intermediate part in the front-back direction (in particular, on a groin part).

A raw material of the intermediate sheet 6 may be any material as long as it has permeability, but a material having hydrophilicity is particularly preferable. By combining such a hydrophilic intermediate sheet 6 with a water-repellent opened front-surface sheet 3 of the present invention, the liquid permeability and reversion prevention performance of the front-surface sheet 3 are remarkably improved. Examples of such a hydrophilic raw material to be used include fiber having hydrophilicity in the raw material itself by using recycled fiber such as rayon or cupra, or natural fiber such as cotton or the like; or fiber imparted with hydrophilicity by surface-treating synthetic fibers such as olefin-based fibers such as of polyethylene and polypropylene, polyester-based fibers, polyamide-based fibers, or composites, copolymers or blend bodies thereof with a hydrophilizing agent. Preferably, a fiber obtained by mixing polyethylene and polypropylene is used. As the fiber that constitutes the nonwoven fabric, any one of a long fiber, a short fiber, or a mixture thereof can be used. The fineness is preferably set at about 3.0 to 7.0 dtex, and preferably at about 4.0 to 6.0 dtex. As the intermediate sheet 6, any of known nonwoven fabrics such as an air through nonwoven fabric, an air laid nonwoven fabric, a spun-bond nonwoven fabric or the like can be used, but the air through nonwoven fabric that does not degrade the air permeability is preferably used.

Furthermore, in the case of an incontinence pad, as described above, in many cases, the incontinence pad is continuously used until the second incontinence. Therefore, it is more preferable to use not a simple hydrophilic nonwoven fabric but a strongly hydrophilic or a durably hydrophilic nonwoven fabric obtained by spraying a strongly hydrophilic agent and/or a durably hydrophilic agent on the nonwoven fabric. The basis weight of the intermediate sheet 6 is 10 to 40 g/m$^2$, and preferably about 18 to 35 g/m$^2$.

In the front-surface sheet 3, in order to prevent the residual liquid of urine and to make a skin trouble such as itchiness or rash difficult to occur during wearing, many openings 10 penetrating from front to back are formed in a region including the excretion hole corresponding part H. Therefore, the intermediate sheet 6 is arranged in a size that covers at least an entire surface of the opening formation region (preferably, when the openings are formed in a region which includes the excretion hole corresponding part H, which is 15% or more of the absorber body length in the length direction of the product and which is 50% or more of the absorber width in the width direction of the product, a size that is 9% or more of the size of the absorber 4 and that covers an entire surface of the opening formation region is desirable).

Adhesion to the front-surface sheet 3 is desirably carried out by a hot-melt adhesive. The kind of the hot-melt adhesive is not limited but an SBS (styrene-butadiene-styrene block copolymer)-based hot-melt adhesive is desirable.

EXAMPLES

[Test 1]

The present invention is an incontinence pad that uses a spunlace nonwoven fabric made of 100% cotton fiber subjected to water repelling treatment as a front-surface sheet and has many openings formed therein. Firstly, a functional evaluation of effects provided by a configuration of the present invention is performed to verify the effects. Evaluation was carried out as follows: 20 women monitors wore and evaluated each product according to four grades, very good: ⊚, good: ○, fair: Δ and poor: ×.

In the test, incontinence pads (total length: 290 mm) defined as a base (Examples 1-1 to 4-2) were produced using front-surface sheets obtained by applying 0.3, 0.5, 1.0, or 1.5 parts by weight of a water repellent agent including beef hydrogenated oil added to stearic acid amide to an opened nonwoven fabric made of 100 parts by weight of non-degreased or degreased cotton fiber (basis weight: 30 g/m$^2$, thickness: 0.35 mm), and using an absorber including a pulp fiber having a basis weight of 370 g/m$^2$, and a superabsorbent polymer having a basis weight of 330 g/m$^2$, in a ratio of the pulp fiber:the superabsorbent polymer=53% by weight:47% by weight, length of 245 mm, and width of 76 mm, where the incontinence pads have a diffusion area of 2000 mm$^2$ or less. In Comparative Examples 1-1 and 1-2, the water repellent agent was not applied and the diffusion area was more than 2000 mm$^2$, which is out of range of the present invention.

Note here that as a second sheet (intermediate sheet), PE/PP 5.6 dtex, air through nonwoven fabric 35 g/m$^2$ (durably hydrophilic) was used in common.

Test results are shown in Table 1.

TABLE 1

| Item | Co. Ex. 1-1 | Co. Ex. 1-2 | Ex. 1-1 | Ex. 1-2 | Ex. 2-1 | Ex. 2-2 | Ex. 3-1 | Ex. 3-2 | Ex. 4-1 | Ex. 4-2 |
|---|---|---|---|---|---|---|---|---|---|---|
| Diffusion area (mm$^2$) | 2558 | 2252 | 1977 | 1719 | 1498 | 1362 | 1450 | 1315 | 1413 | 1295 |
| Application amount of water repellent agent (part by weight) | 0.0 | 0.0 | 0.3 | 0.3 | 0.5 | 0.5 | 1.0 | 1.0 | 1.5 | 1.5 |

TABLE 1-continued

| Item | Co. Ex. 1-1 | Co. Ex. 1-2 | Ex. 1-1 | Ex. 1-2 | Ex. 2-1 | Ex. 2-2 | Ex. 3-1 | Ex. 3-2 | Ex. 4-1 | Ex. 4-2 |
|---|---|---|---|---|---|---|---|---|---|---|
| Degreased or non-degreased | De-greased | Non-degreased | De-greased | Non-degreased | De-greased | Non-degreased | De-greased | Non-degreased | De-greased | Non-degreased |
| Dry feeling after absorption (evaluation after actual use) | | | | | | | | | | |
| Dry feeling before urination | X | X | ○ | ○ | ◎ | ◎ | ◎ | ◎ | ◎ | ◎ |
| Softness of surface sheet before urination | X | X | ○ | ○ | ◎ | ◎ | ◎ | ◎ | ◎ | ◎ |
| Dry feeling immediately after urination | X | X | ○ | ○ | ◎ | ◎ | ◎ | ◎ | ◎ | ◎ |
| Dry feeling after time has passed | X | X | ○ | ○ | ◎ | ◎ | ◎ | ◎ | ◎ | ◎ |

Co. Ex. = Comparative Example,
Ex = Example

In Table 1, when focusing on the relationship between the application amount of the water repellent agent and the diffusion area, although some variation occurs, the diffusion area shows the following trend: without water repellent agent (Comparative Examples 1-1 and 1-2)>0.3 parts by weight of water repellent agent (Examples 1-1 and 1-2)>0.5 parts by weight of water repellent agent (Examples 2-1 and 2-2), 1.0 part by weight of water repellent agent (Examples 3-1 and 3-2)>1.5 parts by weight of water repellent agent (Examples 4-1 and 4-2). Furthermore, when focusing on the relationship between the properties of the cotton fibers (degreased or non-degreased) and the diffusion area, the diffusion area satisfies the following relationship in all cases: degreased cotton fiber>non-degreased cotton fiber.

[Test 2]

In Test 2, absorbers in which the amount of pulp fiber, the amount of polymer, and the ratio thereof are varied respectively were subjected to functional evaluation to verify the effects. Evaluation was carried out as follows: 20 women monitors wore and evaluated each product according to two grades, good: ○, and poor: ×.

In the test, an incontinence pad that uses an opened nonwoven fabric made of 100% by weight non-degreased cotton fiber (basis weight: 30 g/m², thickness: 0.35 mm) in which a water repellent agent obtained by adding beef hydrogenated oil to stearic acid amide applied to a front-surface sheet of the cotton fiber was used. The water repellent agent was applied in 1.5 parts by weight relative to 100 parts by weight of cotton fiber. The diffusion area was 2000 mm² or less.

Note here that as a second sheet (intermediate sheet), PE/PP 5.6 dtex, air through nonwoven fabric 35 g/m² (durably hydrophilic) was used in common.

Test results are shown in Table 2 and Table 3. Note here that "urination amount as standard" in the Tables is a calculated standard of the urine amount that can be absorbed by the absorber 4 based on the pulp amount and polymer amount. Furthermore, regarding "side" and "center" as the emboss in the Tables, side means that the side emboss 21 is provided, and center means that the center emboss 22 is provided.

TABLE 2

| Item | Ex. 5 | Ex. 6 | Ex. 7 | Ex. 8 | Ex. 9 | Ex. 10 | Ex. 11 | Ex. 12 | Ex. 13 | Ex. 14 | Ex. 15 |
|---|---|---|---|---|---|---|---|---|---|---|---|
| Pulp basis weight (g/m²) | 76 | 78 | 102 | 0 | 372 | 372 | 0 | 300 | 800 | 800 | 800 |
| Polymer basis weight (g/m²) | 90 | 175 | 100 | 200 | 160 | 330 | 400 | 800 | 350 | 800 | 560 |
| Ratio of pulp amount (%) | 46 | 31 | 50 | 0 | 70 | 53 | 0 | 27 | 70 | 50 | 59 |
| Ratio of polymer amount (%) | 54 | 69 | 50 | 100 | 30 | 47 | 100 | 73 | 30 | 50 | 41 |
| Product length (mm) | 205 | 205 | 205 | 205 | 290 | 290 | 290 | 360 | 360 | 360 | 630 |
| Absorber length (mm) | 171 | 171 | 171 | 171 | 245 | 245 | 245 | 315 | 315 | 315 | 680 |
| Absorber width (mm) | 65 | 65 | 65 | 65 | 76 | 76 | 76 | 90 | 90 | 90 | 260 |

TABLE 2-continued

| Item | Ex. 5 | Ex. 6 | Ex. 7 | Ex. 8 | Ex. 9 | Ex. 10 | Ex. 11 | Ex. 12 | Ex. 13 | Ex. 14 | Ex. 15 |
|---|---|---|---|---|---|---|---|---|---|---|---|
| Urine amount as standard (cc) | 20 | 30 | 20 | 30 | 80 | 130 | 250 | 300 | 190 | 350 | 2000 |
| Emboss | Side | Side | Side | Side | Center | Center | Center | Center | Center | Center | Center |
| Dry feeling before urination | ○ | ○ | ○ | ○ | ○ | ○ | ○ | ○ | ○ | ○ | ○ |
| Dry feeling immediately after urination | ○ | ○ | ○ | ○ | ○ | ○ | ○ | ○ | ○ | ○ | ○ |
| Dry feeling after time has passed | ○ | ○ | ○ | ○ | ○ | ○ | ○ | ○ | ○ | ○ | ○ |
| Wearing feeling | ○ | ○ | ○ | ○ | ○ | ○ | ○ | ○ | ○ | ○ | ○ |

Ex. = Example

TABLE 3

| Item | Co. Ex. 2 | Co. Ex. 3 | Co. Ex. 4 | Co. Ex. 5 | Co. Ex. 6 | Co. Ex. 7 | Co. Ex. 8 |
|---|---|---|---|---|---|---|---|
| Pulp basis weight (g/m$^2$) | 100 | 155 | 370 | 370 | 650 | 802 | 800 |
| Polymer basis weight (g/m$^2$) | 20 | 30 | 90 | 850 | 150 | 197 | 900 |
| Ratio of pulp amount (%) | 83 | 84 | 80 | 30 | 81 | 80 | 47 |
| Ratio of polymer amount (%) | 17 | 16 | 20 | 70 | 19 | 20 | 53 |
| Product length (mm) | 205 | 205 | 290 | 290 | 360 | 360 | 360 |
| Absorber length (mm) | 171 | 171 | 245 | 245 | 315 | 315 | 315 |
| Absorber width (mm) | 65 | 65 | 76 | 76 | 90 | 90 | 90 |
| Urine amount as standard (cc) | 10 | 15 | 60 | 280 | 120 | 155 | 390 |
| Emboss | Side | Side | Center | Center | Center | Center | Center |
| Dry feeling before urination | ○ | ○ | ○ | ○ | ○ | ○ | ○ |
| Dry feeling immediately after urination | X | X | X | ○ | X | X | ○ |
| Dry feeling after time has passed | X | X | X | ○ | X | X | ○ |
| Wearing feeling | ○ | ○ | ○ | X | ○ | ○ | X |

Co. Ex. = Comparative Example

[Test 3]

In Test 3, cases in which an area per one opening, an opening dimension ratio, a formation region of openings (vertical and horizontal), and an opening rate (%) of the front-surface sheet were each varied were subjected to a functional evaluation to verify the effects. As the evaluation, two kinds of a laboratory evaluation (test room evaluation) and an actual use evaluation were performed. Note here that in the laboratory evaluation, 80 cc of artificial urine was injected in a vicinity of a urination hole, after 5 minutes, a surface of the absorbent article was manually touched and evaluated according to four grades, very good: ⊚, good: ○, fair: Δ and poor: ×. Furthermore, in the actual use evaluation, 20 women monitors wore and evaluated each product according to four grades, very good: ⊚, good: ○, fair: Δ and poor: ×.

The "artificial urine" was a mixture of urea: 2% by weight, sodium chloride: 0.8% by weight, calcium chloride dihydrate: 0.03% by weight, magnesium sulfate heptahydrate: 0.08% by weight, and ion exchange water: 97.09% by weight. Unless otherwise noted, it was used at a temperature of 37° C.

In the test, incontinence pads were produced using front-surface sheets obtained by applying a water repellent agent including beef hydrogenated oil added to stearic acid amide to opened nonwoven fabric made of 100% by weight of non-degreased or degreased cotton fiber (basis weight: 30 g/m$^2$, thickness: 0.35 mm) to a front surface side of cotton fiber in a rate of 1.5 parts by weight of the water repellent agent relative to 100 parts by weight of the cotton fiber, and using absorbers including a pulp fiber having a basis weight of 370 g/m$^2$, and a superabsorbent polymer having a basis weight of 330 g/m$^2$, in a ratio of the pulp fiber:the superabsorbent polymer=53% by weight:47% by weight, where the length of the absorber is 245 mm, the absorber width is 76 mm, and the incontinence pads have a diffusion area of 2000 mm$^2$ or less. In Comparative Example 9, the openings are not provided in the front-surface sheet.

Note here that as a second sheet (intermediate sheet), PE/PP 5.6 dtex, air through nonwoven fabric 35 g/m² (durably hydrophilic) was used in common with size varied.

Test results are shown in Table 4.

TABLE 4

| | Item | Ex. 16 | Ex. 17 | Ex. 18 | Ex. 19 | Ex. 20 | Ex. 21 | Ex. 22 | Ex. 23 | Ex. 24 | Ex. 25 |
|---|---|---|---|---|---|---|---|---|---|---|---|
| | Product length (mm) | 290 | 290 | 290 | 290 | 290 | 290 | 290 | 290 | 290 | 290 |
| | Product width (mm) | 112 | 112 | 112 | 112 | 112 | 112 | 112 | 112 | 112 | 112 |
| | Absorber length (mm) | 245 | 245 | 245 | 245 | 245 | 245 | 245 | 245 | 245 | 245 |
| | Absorber width (mm) | 76 | 76 | 76 | 76 | 76 | 76 | 76 | 76 | 76 | 76 |
| (1) | Area per opening (mm²) | 2.2 | 2.2 | 2.2 | 2.2 | 2.2 | 1.0 | 1.0 | 3.0 | 3.0 | 0.5 |
| | Opening dimension ratio (vertical/lateral) | 2.0 | 2.0 | 2.0 | 2.0 | 2.0 | 1.6 | 1.6 | 1.6 | 1.6 | 1.2 |
| | Dimension of opening region in product length direction (mm) | 245 | 245 | 245 | 245 | 245 | 245 | 245 | 245 | 245 | 245 |
| | Ratio of opening region to absorber length (product length direction including urination hole) (%) | 100 | 100 | 100 | 100 | 100 | 100 | 100 | 100 | 100 | 100 |
| | Dimension of opening region in product width direction (mm) | 76 | 76 | 76 | 76 | 76 | 76 | 76 | 76 | 76 | 76 |
| | Ratio of opening region to absorber width (product width direction including urination hole) (%) | 100 | 100 | 100 | 100 | 100 | 100 | 100 | 100 | 100 | 100 |
| | Opening rate*¹ | 15 | 22 | 45 | 10 | 50 | 15 | 45 | 15 | 45 | 15 |
| (2) | Length of intermediate sheet in product length direction (mm) | 245 | 245 | 245 | 245 | 245 | 245 | 245 | 245 | 245 | 245 |
| | Length of intermediate sheet in product width direction (mm) | 76 | 76 | 76 | 76 | 76 | 76 | 76 | 76 | 76 | 76 |
| | Size of intermediate sheet*² | 100 | 100 | 100 | 100 | 100 | 100 | 100 | 100 | 100 | 100 |
| | (Laboratory evaluation) | | | | | | | | | | |
| | Dry feeling after absorption | ◎ | ◎ | ◎ | ○ | ○ | ◎ | ◎ | ◎ | ◎ | ○ |
| | (Actual use evaluation) | | | | | | | | | | |
| | Dry feeling before urination | ◎ | ◎ | ◎ | ◎ | ◎ | ◎ | ◎ | ◎ | ◎ | ◎ |
| | Dry feeling immediately after urination | ◎ | ◎ | ◎ | ○ | ○ | ◎ | ◎ | ◎ | ◎ | ○ |
| | Dry feeling after time has passed | ◎ | ◎ | ◎ | ○ | ○ | ◎ | ◎ | ◎ | ◎ | ○ |

| | Item | Ex. 26 | Ex. 27 | Ex. 28 | Ex. 29 | Ex. 30 | Ex. 31 | Ex. 32 | Ex. 33 | Ex. 34 | Co. Ex. 9 |
|---|---|---|---|---|---|---|---|---|---|---|---|
| | Product length (mm) | 290 | 290 | 290 | 290 | 290 | 290 | 290 | 290 | 290 | 290 |
| | Product width (mm) | 112 | 112 | 112 | 112 | 112 | 112 | 112 | 112 | 112 | 112 |
| | Absorber length (mm) | 245 | 245 | 245 | 245 | 245 | 245 | 245 | 245 | 245 | 245 |
| | Absorber width (mm) | 76 | 76 | 76 | 76 | 76 | 76 | 76 | 76 | 76 | 76 |
| (1) | Area per opening (mm²) | 0.5 | 0.5 | 4.0 | 4.0 | 2.2 | 2.2 | 2.2 | 2.2 | 2.2 | — |
| | Opening dimension ratio (vertical/lateral) | 1.2 | 1.2 | 2.0 | 2.0 | 2.0 | 2.0 | 2.0 | 2.0 | 2.0 | — |
| | Dimension of opening region in product length direction (mm) | 172 | 172 | 245 | 172 | 123 | 123 | 123 | 123 | 37 | 0 |
| | Ratio of opening region to absorber length (product length direction including urination hole) (%) | 70 | 70 | 100 | 70 | 50 | 50 | 50 | 50 | 15 | 0 |
| | Dimension of opening region in product width direction (mm) | 61 | 61 | 76 | 61 | 53 | 53 | 53 | 53 | 38 | 0 |
| | Ratio of opening region to absorber width (product width direction including urination hole) (%) | 80 | 80 | 100 | 80 | 70 | 70 | 70 | 70 | 35 | 0 |
| | Opening rate*¹ | 45 | 45 | 15 | 45 | 15 | 22 | 22 | 45 | 15 | 0 |
| (2) | Length of intermediate sheet in product length direction (mm) | 180 | 245 | 245 | 180 | 130 | 130 | 245 | 130 | 40 | 245 |
| | Length of intermediate sheet in product width direction (mm) | 67 | 76 | 76 | 67 | 58 | 58 | 76 | 58 | 42 | 76 |
| | Size of intermediate sheet*² | 65 | 100 | 100 | 65 | 40 | 40 | 100 | 40 | 9 | 100 |
| | (Laboratory evaluation) | | | | | | | | | | |
| | Dry feeling after absorption | ○ | ○ | ○ | ○ | ◎ | ◎ | ◎ | ◎ | ◎ | ○ |
| | (Actual use evaluation) | | | | | | | | | | |
| | Dry feeling before urination | ◎ | ◎ | ◎ | ◎ | ◎ | ◎ | ◎ | ◎ | ◎ | ◎ |
| | Dry feeling immediately after urination | ○ | ○ | ○ | ○ | ◎ | ◎ | ◎ | ◎ | ◎ | X |
| | Dry feeling after time has passed | ○ | ○ | ○ | ○ | ◎ | ◎ | ◎ | ◎ | ◎ | X |

*¹The opening rate is a ratio (%) of the total area of openings relative to the entire area of the opening formation region.
*²Size of the intermediate sheet is the ratio (%) with respect to the area of the absorber under the condition of covering the entire surface of the opening formation region.
(1) = Parameters of openings,
(2) = Intermediate sheet
Ex = Example, Co.
Ex. = Comparative Example

REFERENCE SIGNS LIST

1: incontinence pad
2: impermeable back-surface sheet
3: front-surface sheet
4: absorber
5: wrapping sheet
6: intermediate sheet
7: side nonwoven fabric
8: thread-like elastic stretchable member
10: opening
11: vertical streak
12: lateral streak

What is claimed is:

1. An absorbent article for incontinence comprising a front-surface sheet and a back-surface sheet with an absorber interposed therebetween,
wherein the absorbent article for incontinence is an absorbent article for incontinence for medium or larger volume, which absorbs a urine volume of 20 cc or more; and
the front-surface sheet is obtained by applying a water repellent agent to a spunlace nonwoven fabric made of 100% by weight of cotton fiber at an application amount of the water repellent agent of 0.3 to 3.0 parts by weight relative to 100 parts by weight of cotton fiber, has many openings formed in a vertically long shape that is long in the longitudinal direction of the absorbent article for incontinence and penetrating from front to back in a region including an excretion hole corresponding part, has a center emboss extending along the longitudinal direction including the excretion hole corresponding part at a center part in a width direction, the center emboss being a recess-shaped groove that is integrally recessed from the front-surface sheet toward the absorber by compression from an outer-surface side of the front-surface sheet, and has a diffusion area of liquid of 2000 $mm^2$ or less based on a diffusivity test below;
wherein, in the diffusivity test:
(1) two sheets of qualitative filter paper cut into a size of 100 mm×100 mm are stacked on each other, and a front-surface sheet sample cut into a width of 80 mm×a length of 100 mm is placed thereon;
(2) 1 ml of tap water dyed blue is dropped using a pipette from a position 5 mm high from a surface of the front-surface sheet sample;
(3) after allowing to stand for 5 minutes, measurement of a diffusion area of a blue-dyed portion that spreads in the front-surface sheet sample is performed; and
(4) the measurement is performed three times and an average value thereof is calculated.

2. The absorbent article for incontinence according to claim 1, wherein the front-surface sheet is made of non-degreased cotton fiber.

3. The absorbent article for incontinence according to claim 1, wherein the absorber comprises a pulp fiber that does not include synthetic fiber and a superabsorbent polymer in a ratio of the pulp fiber: the superabsorbent polymer as 0 to 70% by weight: 100 to 30% by weight.

4. The absorbent article for incontinence according to claim 3, wherein a basis weight of the pulp fiber is 0 to 800 $g/m^2$, and a basis weight of the superabsorbent polymer is 85 to 800 $g/m^2$.

5. The absorbent article for incontinence according to claim 1, wherein the water repellent agent contains stearic acid amide.

6. The absorbent article for incontinence according to claim 1, wherein the openings are provided in a region that is 15% or more of a length of the absorber in a longitudinal direction of the absorbent article for incontinence, and 50% or more of a width of the absorber in a width direction of the absorbent article for incontinence.

* * * * *